United States Patent [19]
Gaffney et al.

[11] Patent Number: 6,069,142
[45] Date of Patent: May 30, 2000

[54] SYNERGISTIC ANTIMICROBIAL COMBINATION OF 4,5-DICHLORO-2-N-OCTYL-4-ISOTHIAZOLIN-3-ONE AND A MIXTURE OF A CHLORINATED ISOCYANURATE AND A BROMIDE COMPOUND AND METHODS OF USING SAME

[75] Inventors: Tammy W. Gaffney, Mount Lebanon; Christopher L. Wiatr, McMurray, both of Pa.

[73] Assignee: Calgon Corporation, Pittsburgh, Pa.

[21] Appl. No.: 09/220,124

[22] Filed: Dec. 23, 1998

[51] Int. Cl.[7] .......................... A01N 43/66; A01N 43/80; A01N 59/00
[52] U.S. Cl. .......................... 514/241; 424/723; 504/151; 514/372
[58] Field of Search .................. 514/241, 372; 424/723; 504/151

[56] References Cited

U.S. PATENT DOCUMENTS

| | | | |
|---|---|---|---|
| 4,557,926 | 12/1985 | Nelson et al. | 424/19 |
| 5,015,643 | 5/1991 | Jones et al. | 514/241 |
| 5,559,083 | 9/1996 | Kubota et al. | 504/269 |
| 5,648,086 | 7/1997 | Redlich et al. | 424/409 |
| 5,703,105 | 12/1997 | Redlich et al. | 514/372 |
| 5,730,907 | 3/1998 | Schultz et al. | 252/400.62 |
| 5,756,526 | 5/1998 | Williams et al. | 514/373 |

FOREIGN PATENT DOCUMENTS

| | | |
|---|---|---|
| 0 490 567 B1 | 9/1996 | European Pat. Off. . |
| 0 476 943 B1 | 10/1996 | European Pat. Off. . |
| 0 611 522 B1 | 1/1997 | European Pat. Off. . |
| 0 615 688 B1 | 11/1997 | European Pat. Off. . |
| 0 608 912 B1 | 6/1998 | European Pat. Off. . |
| WO 93/04987 | 3/1993 | WIPO . |

*Primary Examiner*—Allen J. Robinson
*Attorney, Agent, or Firm*—Diane R. Meyers; Eckert Seamans Cherin & Mellott, LLC

[57] ABSTRACT

Synergistic antimicrobial combinations comprising 4,5-dichloro-2-N-octyl-4-isothiazolin-3-one and a mixture of a chlorinated isocyanurate and a bromide compound are disclosed. Methods for inhibiting microbial growth using these synergistic antimicrobial combinations are also disclosed.

20 Claims, No Drawings

SYNERGISTIC ANTIMICROBIAL COMBINATION OF 4,5-DICHLORO-2-N-OCTYL-4-ISOTHIAZOLIN-3-ONE AND A MIXTURE OF A CHLORINATED ISOCYANURATE AND A BROMIDE COMPOUND AND METHODS OF USING SAME

FIELD OF THE INVENTION

The present invention relates to synergistic antimicrobial compositions which are generally useful for inhibiting microbial growth wherever such microbial growth is found, for example, in aqueous systems related to a wide variety of industrial applications. More particularly, the present invention relates to synergistic admixtures of 4,5-dichloro-2-N-octyl-4-isothiazolin-3-one and a mixture of a chlorinated isocyanurate and a bromide compound. Methods for using the same are also disclosed.

BACKGROUND OF THE INVENTION

Both 4,5-dichloro-2-N-octyl-4-isothiazolin-3-one, referred to herein as DOI, and the combination of a chlorinated isocyanurate and a bromide compound, referred to herein as Towerbrom®, are known individually as antimicrobial and/or disinfecting agents. The unexpected finding of the present invention is that they are synergistic when used in combination. As used herein, the terms "synergy" and "synergistic" refer to instances where the effectiveness of a composition comprising two or more biocides, such as DOI and Towerbrom®, exceeds the sum of the efficacies of the individual components taken alone. Thus, using a synergistic biocidal combination may allow for use of a lower overall concentration of biocide or the realization of an enhanced antimicrobial effect at a comparable dosage.

Both Towerbrom®, and related compounds, and DOI, and related compounds, are known in the art as antimicrobial agents, both alone and in conjunction with other biocides. The synergistic combination of Towerbrom® and DOI, however, is not taught or suggested in the art. For example, chlorinated isocyanurates, alone or in combination with sodium bromide and/or potassium bromide, have been reported as disinfecting agents in PCT Application Number WO 93/04987, and U.S. Pat. Nos. 4,557,926 and 5,015,643. In addition, U.S. Pat. No. 5,254,526 discloses a method of inhibiting the growth of algae by introducing to the body of water being treated a chlorine-containing oxidizer and a water soluble bromide which has been premixed with an alkali metal, alkaline earth metal or ammonium polyphosphate.

Using microbicidal compositions of DOI either alone or in conjunction with other compounds, as well as the use of other isothiazoline compounds as microbicides, is reported, for example, in EP 608 912; EP 615 688; EP 611 522; EP 476 943; and U.S. Pat. Nos. 5,756,526; 5,730,907; 5,703,105; 5,648,086; and 5,559,083. European Patent 490 567 reports the use of halogen-containing organic stabalizers for 3-isothiazolines, including trichloroisocyanuric acid or other halogenated compounds. Methods of preventing or inhibiting the growth of microorganisms is also reported. The patent does not appear to teach the use of a chlorinated isocyanurate in conjunction with a bromide compound in a synergistic mixture with isothiazolines.

As used herein, the phrases "antimicrobial", "biocide", and "inhibiting microbial growth" refer to the killing of, the inhibition of, or the control of the growth of bacteria, yeast, mold, and/or algae. A number of important industries have experienced serious adverse effects from the activity of such biological growth on the raw materials which they employ, in their process waters, on various components of their manufacturing processes, and in the finished products which they produce. Such industries include the paint, wood, textile, cosmetic and personal care, leather, tobacco, fur, rope, paper, pulp, plastics, fuel, oil, rubber, and machine industries.

Systems which utilize circulating water or aqueous media become infected with microorganisms and experience substantial impairment of their efficiency when deposits of the microorganisms build up in the system. The deposits coat the walls of tanks and other vessels and any machinery or processing equipment which is employed and create blockages in pipes and valves. The deposits also create discolorations and other imperfections in the products being produced, forcing costly shutdowns. Control of microorganisms is particularly important in aqueous media in which there are dispersed particles or fines in the aqueous media, for example, dispersed cellulosic fibers and dispersed fillers and pigments in papermaking, and dispersed pigments in paint manufacture.

It is contemplated that the synergistic admixture of Towerbrom® and DOI as disclosed herein, and the methods for using the same, will be useful in virtually any aqueous system or on any article or product of manufacture in which inhibition of microbial growth is desired, absent compatibility problems. Important applications of the synergistic antimicrobial combinations of the present invention include, for example: inhibiting the growth of bacteria and fungi, including yeast and mold, in aqueous paints, adhesives, latex emulsions, inks and joint cements; preserving wood; preserving cutting oils and metal working fluids; controlling slime-producing bacteria and fungi, including yeast and mold, in pulp and paper mills and cooling towers; as a spray or dip treatment for textiles and leather to prevent mold growth; as a component of anti-fouling paints to prevent adherence of fouling organisms; protecting paint films, especially exterior paints, from attack by fungi which occurs during weathering of the paint film; protecting processing equipment from slime deposits during manufacture of cane and beet sugar, foods, foodstuffs and food additives; preventing microorganism buildup and deposits in air washer or scrubber systems and in industrial fresh water supply systems; controlling microorganism contamination in closed loop and recirculating water cooling systems; controlling microorganism contamination and deposits in oil field drilling fluids and muds, and in secondary petroleum recovery processes; preventing bacterial and fungal growth in paper coating processes which might adversely affect the quality of the paper coating; controlling bacterial and fungal growth and deposits during the manufacture of various specialty boards, e.g., cardboard and particle board; preventing sap stain discoloration on freshly cut wood of various kinds; controlling bacterial and fungal growth in clay and pigment slurries of various types which are manufactured for later use in paper coating and paint manufacturing and which are susceptible to degradation by microorganisms during storage and transport; as a hard surface disinfectant to prevent growth of bacteria and fungi on walls, floors, etc.; and in swimming pools to prevent algal growth.

Slime control in papermaking processes is also of particular importance. The control of bacteria and fungi in pulp and paper mill water systems which contain aqueous dispersions of papermaking fibers in various consistencies is especially critical. The uncontrolled buildup of slime produced by the accumulation of bacteria and fungi may cause off-grade production, decreased production due to downtime and greater cleanup frequency, increased raw material usage, and increased maintenance costs. The problem of slime deposits is especially critical in light of the widespread use of closed white water systems in the paper industry.

Another important area that requires the use of good antimicrobial compositions to control bacterial and fungal growth is in clay and pigment slurries. These slurries comprise various clays (e.g., kaolin) and pigments (e.g., calcium carbonate and titanium dioxide) and usually are manufactured at a location separate from the end use application. This means that they are generally transported and stored for later use at the application site. Because of high quality standards for the paper and paint products in which such slurries are used, it is essential that these clay or pigment slurries have a very low microorganism count per gram of sample.

There remains a very real and substantial need for antimicrobial compositions capable of effectively controlling and/or inhibiting microbial growth in industrial aqueous systems and on articles of manufacture. Because of increasing environmental regulations, there is still a further need to provide biocidal compositions having enhanced antimicrobial effect which are effective in lower doses than historically used. Use of lower amounts of biocides has a favorable impact on the environment, and allows users to realize significant cost savings.

SUMMARY OF THE INVENTION

The present invention generally meets the above described needs by providing synergistic antimicrobial combinations comprising 4,5-dichloro-2-N-octyl-4-isothiazolin-3-one (DOI) and a mixture of a chlorinated isocyanurate and a bromide compound (Towerbrom®). The composition can be in any form, such as an aqueous concentrate or a dilute working solution. The present invention also provides a method for inhibiting microbial growth in aqueous systems and on articles of manufacture prone to such growth, comprising adding to said systems, or applying to said articles, an effective amount of DOI and Towerbrom®.

DESCRIPTION OF THE INVENTION

The present invention is directed to a synergistic antimicrobial composition comprising: a) 4,5-dichloro-2-N-octyl-4-isothiazolin-3-one, and b) a mixture of i) a chlorinated isocyanurate and ii) a bromide compound wherein the weight ratio of a) to b), on an active basis, ranges from about 1:1 to 1500:1. Preferably, this ratio will be in an amount of 5:1 to 1220:1, more preferably between about 10:1 and 80:1. The composition can also be in the form of a dilute solution or an aqueous concentrate, further comprising water or other solvents, as is more fully discussed below. The present invention is further directed to a method for inhibiting microbial growth in an aqueous system or on an article of manufacture prone to such growth, which method comprises treating said system or said article with an effective amount of an antimicrobial combination of: a) 4,5-dichloro-2-N-octyl-4-isothiazolin-3-one, and b) a mixture of i) dichloroisocyanuric acid and ii) sodium bromide wherein the weight ratio of a) to b), on an active basis, ranges from about 1:1 to 1500:1.

As used herein, the term "effective amount" refers to that amount of a composition comprising DOI and Towerbrom® necessary to achieve the desired level of inhibition or control of microbial growth in the aqueous system or on the article being treated. Preferably, this amount is an amount that results in a synergy index ("K" value) of less than 1 after partial biocide degradation. Determination of K value is discussed in the Example section below.

The active ingredients of the synergistic antimicrobial compositions of the present invention may be used in diverse formulations: solid, including finely divided powders and granular materials; and liquid, such as solutions, emulsions, suspensions, concentrates, emulsifiable concentrates, slurries and the like, depending upon the application intended, and the formulation media desired. Further, when the synergistic antimicrobial combinations are liquid, they may be employed neat or may be incorporated into various formulations, both solid and liquid, as an adsorbate on suitable inert carriers such as talc, clays, diatomaceous earth and the like, or water and various organic liquids such as lower alkanols, kerosene, benzene, toluene, and other petroleum distillate fractions or mixtures thereof. DOI is available from Rohm and Haas, Philadelphia, Pa. in liquid form as a 4.0% active solution as Klarix® 4000.

It is preferred that the a chlorinated isocyanurate and a bromide compound components be used as a single composition. It is also within the scope of the invention, however, to use them separately. As used herein, the term "chlorinated isocyanurate" includes, for example, chlorinated isocyanuric acids including but not limited to dichloroisocyanuric acid, trichloroisocyanuric acid, the alkali metal salts of these acids, hydrates, complexes and mixtures of these acids or their salts, halogenated hydantoins, halogenated alkyl halohalides and halogenated methyl hypochloride. Sodium dichloroisocyanurate (anhydrous) and trichloroisocyanuric acid are preferred for the present methods, with dichloroisocyanuric acid being most preferred. Suitable bromide compounds include, but are not limited to, alkali bromides such as sodium bromide, magnesium bromide, calcium bromide or potassium bromide; alkaline earth metal bromides; R4-ammonium bromides where R is an alkyl or aryl group; bromamines; and N-brominated organic compounds. Sodium bromide is the preferred bromide compound. It is also within the scope of the present invention to employ other halide compounds, such as iodide.

The weight ratio of chlorinated isocyanurate to bromide compound should be at least about 3:1, on an active basis, and preferably ranges from about 5:1 to about 20:1 more preferably about 5:1 to about 19:1, most preferably between about 12:1 and 13.5:1. In the most preferred case, the chlorinated isocyanurate compromises about 85–95% by weight, on an active basis, of a chlorinated isocyanurate/bromide composition and the bromide compound about 5–15% by weight, on an active basis, of the composition. Additionally, the chlorinated isocyanurate/bromide composition may comprise a measurable percentage, but generally not in excess of about 5% by weight on an active basis, of inert impurities or fillers such as sodium chloride and water. Sodium dichloroisocyanurate (anhydrous) together with sodium bromide is preferred.

Products meeting the above specifications are commercially available from the OxyChem Corporation under the names Towerbrom® 60M and Towerbrom® and from Calgon Corporation under the names Towerbrom® 960, Towerbrom® 993 and Towerbrom® 991. The Towerbrom® 60M and 960 products comprise about 89% sodium dichloroisocyanurate (anhydrous), about 7% sodium bromide and about 4% inert ingredients, with all of the percentages given by weight, on an active basis. The Towerbrom® 90M, 993 and 991 products comprise about 92–93% trichloroisocyanuric acid, about 7% sodium bromide and about 1% or less active ingredients, with all of the percentages given by weight, on an active basis. The commercially available Towerbrom® 60M and 960 products discussed above are in dry, granular form. As used herein, the term "granular" means virtually any particle size ranging from powders to coarse granules, as generally understood by those skilled in the art. The Towerbrom® 90M and 993 products come in three inch tablets, while 991 is a one inch tablet. It will be further understood by those skilled in the art that the form of the product and size of the particle are generally unimportant relative to the methods and compositions of the present invention. While Towerbrom® and similar products have been used as antimicrobial agents in cooling towers, heat exchangers, industrial water scrubbing systems and the like, use of these products as antimicrobial agents in a synergistic admixture with DOI was previously unknown.

Biocides and other antimicrobial compositions typically fall into two categories, oxidizing and non-oxidizing. It will be appreciated by those skilled in the art that the present synergistic admixture combines both an oxidizing biocide, namely the Towerbrom®, and a non-oxidizing biocide, namely the DOI. Such a combination allows for more thorough microorganism control. For example, in cooling tower applications the present methods provide control of both heterotrophic organisms and algal deposits.

In accordance with the present invention, the weight ratio of the two components of the synergistic combination are dictated by the dosage levels of each component which demonstrate synergism, based on 100% active ingredient, relative to each end use application. Typically, the weight ratio of component a) DOI, and component b), Towerbrom®, ranges from about 1:1 to 1500:1 on an active to active basis, preferably from about 5:1 to 1220:1, more preferably from about 10:1 to 80:1. As will be understood by one skilled in the art, however, the synergistic weight ratio of the two components generally varies to some extent depending on the application and the organism being controlled. For example, a higher ratio of Towerbrom® to DOI might be more effective in one application, while a higher ratio of DOI to Towerbrom® might be more effective in another application.

An effective amount of a synergistic combination of Towerbrom® and DOI should be added to the aqueous system being treated. At least 0.1 parts per million (ppm), based on the weight of water in the system being treated, of the synergistic combination described above is added. Preferably, between about 0.05 ppm and about 1000 ppm of Towerbrom® and between about 0.01 ppm and 10 ppm of DOI, based on the weight of water in the system being treated, are added. It is well within the ordinary skill of one practicing in the art to determine the effective amount of biocide for a given system based on various system parameters including but not limited to the size of the system, pH of the system, the types of organisms present and the amount of control desired.

Likewise, an effective amount of a synergistic combination of Towerbrom® and DOI should be applied to the article of manufacture being treated. Generally, a solution of the synergistic antimicrobial combination described above having a concentration of at least 0.1 ppm is incorporated into, sprayed onto, used to dip, or otherwise applied to the substrate being treated in order to prevent growth of bacteria, mold, yeast and algae. Again, it is well within the ordinary skill of one practicing in the art to determine the effective amount of biocide to apply to a given article of manufacture being treated.

The upper limits of each component and the upper limits of the total synergistic combination of the present invention depend upon the needs and desires of the user taking into account, for example, economics and environmental concerns. The total amount of the inventive synergistic biocide combination present in an aqueous system can be less than about 300 ppm, preferably less than about 200 ppm, more preferably no more than about 150 ppm, with an amount no more than about 100 ppm being most preferred. As noted above, one skilled in the art can determine the effective amount of biocide for a given system based on various system parameters.

Additionally, in some applications a higher overall percent biocide is required to control or kill the microbes. In these applications, higher amounts of each biocide can be used while maintaining a measurable synergistic effect. Thus, the upper limit of the synergy of the combination varies, depending on the application. In preservation applications for example, each biocide in the blend could be present in a concentration ranging from about 0.05 ppm up to as high as 1000 ppm.

Much higher amounts of one or both biocides can be used in the system or on the article to provide protection from microbial growth since the concentration throughout the entire system or article will not necessarily be the same and the localized ratios can vary widely. Also, initial higher amounts can be added with the anticipation that one or both biocides will degrade or decompose over time to then be within the ranges stated above. Even though higher amounts than stated above are used with the system/article to be treated, what is important is that the localized amounts or time degraded amounts fall within the stated range at some point in time, thereby benefiting from the synergistic combination as the microbes in the system are controlled.

To prepare a synergistic composition under this invention an effective amount of each active ingredient should be combined in a suitable carrier such as water, organic solvents, and the like. The preparation of such a composition is within the ordinary skill of one practicing in the art.

Thus, the synergistic antimicrobial combination of the present invention can also comprise a third component, c), which is a solvent. Such a solution would comprise: a) about 10 to about 50 weight percent DOI; b) about 1 to about 5 weight percent of Towerbrom®; c) the remainder solvent; wherein the weight ratio of a) to b), on an active basis, ranges between about 2:1 and 50:1. Any suitable organic or inorganic solvent or water can be used absent compatibility problems with the system or article being treated.

Alternatively, the synergistic antimicrobial combination according to the present invention can also be an aqueous concentrate that comprises much higher levels of each active ingredient.

It will also be understood by one skilled in the art that the synergistic antimicrobial combination disclosed herein may be used in combination with other antimicrobial materials. For example, the combination can be combined with other fungicides and bactericides in appropriate concentrations and in appropriate instances so as to combine the action of each to obtain particularly useful results. Such combinations might find particular application in the preparation of germicidal soaps, in the production of cosmetics and aqueous coatings and in combating paper mill slime accumulations. The synergistic antimicrobial combination of the present invention can be combined with other algicidal agents as well.

In accordance with the present invention there is still further provided a method of inhibiting the growth of at least one of: bacteria, yeast, mold and algae. According to the methods of the present invention, this growth is inhibited in aqueous systems or on articles or products of manufacture prone to such growth. These methods comprise adding to the aqueous system or treating the article or product containing said bacteria, yeast, mold and/or algae with an effective amount of a synergistic combination of Towerbrom® and DOI. This addition can be accomplished either by simple addition of Towerbrom® and DOI together as a single admixture, or by addition of the two components separately. As noted above, the Towerbrom® itself can be added as a single mixture or by addition of the two components, a chlorinated isocyanurate and a bromide compound, separately. Such separate administration can either be at the same time or at different times. The net effect will be the same—the system, article or product being treated will ultimately have incorporated therein or have applied thereto the desired dosage concentration of each component.

It is contemplated that the synergistic admixture of 4,5-dichloro-2-N-octyl-4-isothiazolin-3-one and dichloroisocyanuric acid and sodium bromide, as disclosed herein, and the methods for using the same, will be useful in virtually any aqueous system or on any article or product of manufacture in which inhibition of microbial growth is desired, absent compatibility problems. Suggested applications of the synergistic antimicrobial combinations of the present invention include, for example: inhibiting the growth of bacteria and fungi in aqueous paints, adhesives, latex emulsions, inks, joint cements and caulking compounds; preserving wood; preserving cutting oils and metal working fluids; controlling slime-producing bacteria and fungi, including yeast and mold, in pulp and paper mills and cooling towers; as a spray or dip treatment for textiles and leather to prevent mold growth; as a component of antifouling paints to prevent adherence of fouling organisms; protecting paint films, especially exterior paints, from attack by fungi which occurs during weathering of the paint film; protecting processing equipment from slime deposits during manufacture of cane and beet sugar, food, foodstuffs and food additives; preventing microorganism buildup and deposits in air washer or scrubber systems and in industrial fresh water supply systems; controlling microorganism contamination in closed loop and recirculating water cooling systems; controlling microorganism contamination and deposits in oil field drilling fluids and muds, and in secondary petroleum recovery processes; preventing bacterial and fungal growth in paper coating processes which might adversely affect the quality of the paper coating; controlling bacterial and fungal growth and deposits during the manufacture of various specialty boards, e.g., cardboard, particle board and food grade board; preventing sap stain discoloration on freshly cut wood of various kinds; controlling bacterial and fungal growth in clay and pigment slurries of various sypes which are manufactured for later use in paper coating and paint manufacturing and which are susceptible to degradation by microorganisms during storage and transport; as a hard surface disinfectant to prevent growth of bacteria and fungi on walls, floors, etc.; in swimming pools to prevent algal growth, including green algae and cyanobacteria (blue green algae); and to control bacterial and fungal growth in various cosmetic products. It is further contemplated that the synergistic admixture of the present invention will be useful in various types of non-aqueous systems as well.

Any system which utilizes circulating water or aqqueous media that becomes infected with microorganisms and experiences substantial impairment of their efficiency when deposits of the microorganisms build up in the system and can be treated according to the present invention. Control of microorganisms by the present invention in aqueous media is particularly important where there are dispersed particles or fines in the aqueous media, for example, dispersed cellulosic fibers and dispersed fillers and pigments in papermaking, and dispersed pigments in paint manufacture.

The compositions of the present invention are believed to be effective regardless of the method of application. For example, the antimicrobial compositions described herein can be added to a system being treated via a low level, continuous feed practice, a semi-continuous feed practice or through slug feeding. All of these feeding practices will be familiar to one having ordinary skill in the art. Preferably, addition of the Towerbrom® is through either continuous or slug feeding, while addition of DOI is through slug feeding. It will be understood that either kind of feed for each of the components can be used based upon the needs and desires of the user. In a recirculating water system, slug feeding allows the user to monitor the microorganism concentration in the system, and feed product only when microorganism concentrations increase; the user realizes a cost savings by feeding an effective amount of Towerbrom® and DOI only when needed. Typically, when treating a paint, a slug feed should be incorporated in the pigment grind; when treating an emulsion, adhesive or similar product, a slug feed should be added with the water used in the product formulation or as a post additive at the end of the manufacturing process.

As noted above, the present invention is based upon the discovery that use of Towerbrom® in conjunction with DOI produces synergistic results and is effective in controlling the growth of bacteria, fungi and algae in a variety of industrial and other applications. The utility of the synergistic antimicrobial combination disclosed herein derives from its versatility both in the numerous industries in which it can be applied, as well as the numerous microorganisms against which it is effective.

The superior antimicrobial activity of the synergistic antimicrobial combination of Towerbrom® and DOI has been confirmed using standard laboratory techniques. The antimicrobial combination will be effective, for example, in inhibiting fungal growth including but not limited to the yeasts *Candida albicans, Saccharomyces cerevisiae* and the mold *Aspergillus niger*, bacteria, such as *Klebsiella pneumoniae, Escherichia coli, Pseudomonas aeruginosa*, Bacillus sp., Staphylococcus sp., Flavobacterium sp., Enterobacter sp., and Xanthomonas sp., other aerobic bacteria, anaerobic bacteria, other fresh water organisms such as filamentous bacteria, other fungi including but not limited to other species of Candida and Saccharomyces and white and pink yeasts, and various species of green algae and blue-green algae including but not limited to various species of Cyanobacterium.

EXAMPLES

The following examples are set forth to illustrate the present invention and should not be construed as limiting the invention in any way.

Example 1

The biocidal efficacy in microtiter tests of the antimicrobial composition of the present invention is demonstrated below using *Pseudomonas aeruginosa*.

An 4× stock solution of DOI was prepared by dissolving about 2.56 grams (g) of 2.0% active DOI in about 100 ml of deionized water. The DOI used in the examples was obtained from Rohm and Haas, Philadelphia, Pa., as XB-3.

An 8× stock solution of Towerbrom® was prepared by dissolving about 0.2048 g of approximately 100% active Towerbrom® powder in about 1000 ml of deionized water. The Towerbrom® was obtained from Calgon Corporation, Pittsburgh, Pa. as Towerbrom® 960. The stock solution was stirred for about 30 minutes prior to use.

Duplicate microtiter plates were prepared for use in the example; each microtiter plate had 8 rows, A–H, and 12 columns, 1–12. The concentration of each biocide in each well of the plates is depicted below. The concentration of DOI is given in ppm active ingredient, while the concentration of Towerbrom® is given in ppm of product.

TABLE 1 ip 05182523.31

| ROW LETTER | BIOCIDE | AMOUNT OF EACH BIOCIDE IN WELLS OF EACH MICROTITER PLATE CONCENTRATIONS | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| A | DOI | 128 | 128 | 128 | 128 | 128 | 128 | 128 | 128 | 128 | 128 | 128 | — |
|   | Towerbrom ® | 25.6 | 12.8 | 6.4 | 3.2 | 1.6 | 0.8 | 0.4 | 0.2 | 0.1 | 0.05 | 0 | — |
| B | DOI | 64 | 64 | 64 | 64 | 64 | 64 | 64 | 64 | 64 | 64 | 64 | — |
|   | Towerbrom ® | 25.6 | 12.8 | 6.4 | 3.2 | 1.6 | 0.8 | 0.4 | 0.2 | 0.1 | 0.05 | 0 | — |
| C | DOI | 32 | 32 | 32 | 32 | 32 | 32 | 32 | 32 | 325 | 32 | 32 | — |
|   | Towerbrom ® | 25.6 | 12.8 | 6.4 | 3.2 | 1.6 | 0.8 | 0.4 | 0.2 | 0.1 | 0.05 | 0 | |
| D | DOI | 16 | 16 | 16 | 16 | 16 | 16 | 16 | 16 | 16 | 16 | 16 | — |
|   | Towerbrom ® | 25.6 | 12.8 | 6.4 | 3.2 | 1.6 | 0.8 | 0.4 | 0.2 | 0.1 | 0.05 | 0 | — |
| E | DOI | 8 | 8 | 8 | 8 | 8 | 8 | 8 | 8 | 8 | 8 | 8 | — |
|   | Towerbrom ® | 25.6 | 12.8 | 6.4 | 3.2 | 1.6 | 0.8 | 0.4 | 0.2 | 0.1 | 0.05 | 0 | — |
| F | DOI | 4 | 4 | 4 | 4 | 4 | 4 | 4 | 4 | 4 | 4 | 4 | — |
|   | Towerbrom ® | 25.6 | 12.8 | 6.4 | 3.2 | 1.6 | 0.8 | 0.4 | 0.2 | 0.1 | 0.05 | 0 | — |
| G | DOI | 2 | 2 | 2 | 2 | 2 | 2 | 2 | 2 | 2 | 2 | 2 | — |
|   | Towerbrom ® | 25.6 | 12.8 | 6.4 | 3.2 | 1.6 | 0.8 | 0.4 | 0.2 | 0.1 | 0.05 | 0 | — |
| H | DOI | 0 | 0 | 0 | 0 | 0 | 0 | 0 | 0 | 0 | 0 | 0 | — |
|   | Towerbrom ® | 25.6 | 12.8 | 6.4 | 3.2 | 1.6 | 0.8 | 0.4 | 0.2 | 0.1 | 0.05 | 0 | — |

As is illustrated in the table above, the amounts of DOI and Towerbrom® were varied in a serial dilution ranging from 128 ppm active to 2 ppm active for DOI and 25.6 ppm product to 0.05 ppm product for Towerbrom®. Column 11 represents use of DOI alone, while Row H represents use of Towerbrom® alone. Column 12 was a broth control performed to ensure there was no contamination of the microtiter plates.

An indirect microtiter was performed in which the biocides and organisms were initially added to sterile phosphate buffer in the microtiter plate containing the biocide concentrations given above. Because turbidity (organism growth) cannot be observed in the buffer, it was necessary to subculture each of the wells into a broth. Accordingly, at designated times (18 and 24 hours) the microtiter wells were subcultured into another plate containing Trypticase Soy Broth. The plates were incubated and read on a plate reader. A direct correlation between the bacterial growth in the broth and buffer can be made according to this method.

To prepare the P. aeruginosa, the bacteria was subcultured onto a plate of Standard Method Agar and incubated overnight at 35° C. The inoculum was prepared by making a 0.5 MacFarland standard in 10 ml sterile phosphate buffer (Butterfields). The MacFarland was diluted in 90 ml sterile Butterfields buffer.

The plates were incubated for 18 hours at 35° C., then 10 μl from each well were subcultured into 200 μl of Trypticase Soy Broth in another microtiter plate. This subculturing was repeated at 24 hours in a separate plate. The 18 and 24 hour subculture plates were incubated at 35° C. overnight and read the next day on a Dynatech MR-5000 micro plate reader, available from Dynatech Laboratories, Chantilly, Va., the use of which will be familiar to one having ordinary skill in the art. The total aerobic plate count of P. aeruginosa inoculum was $1.0 \times 10^7$ cfu/ml.

Microtiter plates were then subcultured from the phosphate buffer plates at 18 and 24 hours following biocide addition. Subculturing was done to determine the minimum biocidal concentration (MBC). The MBC is the lowest concentration of biocide that results in no growth after subculturing and subsequent incubation.

Following an overnight incubation period at 35° C., the presence or absence of growth in each well of the plates was determined. Growth in the microtiter plates was determined with the Dynatech MR-5000 microplate reader. The presence or absence of growth in each well, along with the concentration of biocide in each well, was then used to determine the synergistic properties of the biocide combinations. The synergistic properties were evaluated by determining the Kull value, or K value.

The method for calculating K value is well known to those skilled in the art. In this example, the K value was determined by the following formula:

$$K = \frac{[DOI] \text{ In Combination}}{[DOI] \text{ Alone}} + \frac{[\text{Towerbrom}^®] \text{ In Combination}}{[\text{Towerbrom}^®] \text{ Alone}}$$

where "[DOI] In Combination" means the concentration of DOI which, when used in combination with Towerbrom®, resulted in inhibition of microbial growth; "[Towerbrom®] In Combination" means the concentration of Towerbrom® which, when used in combination with DOI, resulted in inhibition of microbial growth; "[DOI] Alone" means the concentration of DOI which, when used alone, resulted in inhibition of microbial growth; and "[Towerbrom®] Alone" means the concentration of the Towerbrom® which, when used alone, resulted in inhibition of microbial growth.

A K value of less than 1 indicates synergy between the two biocides, a K value of greater than 1 indicates antagonism between the two biocides, and a K value equal to 1 indicates an additive effect of the two biocides.

The K values determined for each microtiter plate are recorded in Tables 2–5 below.

TABLE 2

"K" VALUES OBTAINED FOR P. AERUGINOSA IN PLATE 1 (18 HR.)

| [DOI] Alone, ppm | [Towerbrom ®] Alone, ppm | [DOI] In Combination, ppm | [Towerbrom ®] In Combination, ppm | K Value | Weight Ratio Towerbrom ®:DOI |
|---|---|---|---|---|---|
| 16 | 0.8 | 8 | 0.2 | 0.75 | 1:20 |
| 16 | 0.8 | 4 | 0.4 | 0.75 | 1:10 |
| 16 | 0.8 | 2 | 0.4 | 0.625 | 1:5 |

TABLE 3

"K" VALUES OBTAINED FOR P. AERUGINOSA IN PLATE 2 (18 HR.)

| [DOI] Alone, ppm | [Towerbrom ®] Alone, ppm | [DOI] in Combination, ppm | [Towerbrom ®] in Combination, ppm | K Value | Weight Ratio Towerbrom ®:DOI |
|---|---|---|---|---|---|
| 32 | 0.8 | 16 | 0.05 | 0.5625 | 1:1220 |
| 32 | 0.8 | 16 | 0.1 | 0.625 | 1:160 |
| 32 | 0.8 | 8 | 0.2 | 0.5 | 1:40 |
| 32 | 0.8 | 4 | 0.4 | 0.625 | 1:10 |
| 32 | 0.8 | 16 | 0.2 | 0.75 | 1:80 |
| 32 | 0.8 | 8 | 0.4 | 0.75 | 1:20 |

TABLE 4

"K" VALUES OBTAINED FOR P. AERUGINOSA IN PLATE 1 (24 HR.)

| [DOI] Alone, ppm | [Towerbrom ®] Alone, ppm | [DOI] In Combination, ppm | [Towerbrom ®] In Combination, ppm | K Value | Weight Ratio Towerbrom ®:DOI |
|---|---|---|---|---|---|
| 16 | 0.8 | 8 | 0.2 | 0.75 | 1:40 |
| 16 | 0.8 | 4 | 0.4 | 0.75 | 1:10 |
| 16 | 0.8 | 2 | 0.4 | 0.625 | 1:5 |

TABLE 5

"K" VALUES OBTAINED FOR P. AERUGINOSA IN PLATE 2 (24 HR.)

| [DOI] Alone, ppm | [Towerbrom ®] Alone, ppm | [DOI] In Combination, ppm | [Towerbrom ®] In Combination, ppm | K Value | Weight Ratio Towerbrom ®:DOI |
|---|---|---|---|---|---|
| 16 | 0.8 | 8 | 0.2 | 0.75 | 1:40 |
| 16 | 0.8 | 4 | 0.4 | 0.75 | 1:10 |

As can be seen from the results shown in Tables 2–5, the "K" values obtained when testing P. aeruginosa were below 1 at the concentrations indicated; this demonstrates synergy between the two biocides. Synergy was seen at ratios of Towerbrom®:DOI ranging from 1:5 to 1:1220.

Whereas particular embodiments of this invention have been described above for purposes of illustration, it will be evident to those skilled in the art that numerous variations of the details of the present invention may be made without departing from the invention as defined in the appended claims.

What is claimed is:

1. A synergistic antimicrobial combination comprising:
   a) 4,5-dichloro-2-N-octyl-4-isothiazolin-3-one; and
   b) a mixture of i) a chlorinated isocyanurate and ii) a bromide compound; wherein the weight ratio of a) to b), on an active basis, ranges between about 1:1 and 1500:1, and the weight ratio of i) to ii), on an active basis, ranges between about 3:1 and 20:1.

2. The combination of claim 1, wherein the weight ratio of a) to b) ranges between about 5:1 and 1220:1, and the weight ratio of i) to ii) ranges between about 5:1 and 19:1.

3. The combination of claim 2, wherein the weight ratio of a) to b) ranges between about 10:1 and 80:1 and the weight ratio of i) to ii) ranges between about 12:1 and 13.5:1.

4. The combination of claim 1, wherein said chlorinated isocyanurate is dichloroisocyanurate and said bromide compound is sodium bromide.

5. A method for inhibiting microbial growth in an aqueous system which comprises adding to said system an effective amount of a synergistic antimicrobial combination comprising:
   a) 4,5-dichloro-2-N-octyl-4-isothiazolin-3-one; and
   b) a mixture of i) a chlorinated isocyanurate and ii) a bromide compound; wherein the weight ratio of a) to b), on an active basis, ranges between about 1:1 and 1500:1, and the weight ratio of i) to ii), on an active basis, ranges between about 3:1 and 20:1.

6. The method of claim 5, wherein the weight ratio of a) to b), on an active basis, ranges between about 5:1 and 1220:1; and the weight ratio of i) to ii) ranges between about 5:1 and 19:1.

7. The method of claim 5, wherein component a) and component b) are added together as a single composition to the system being treated.

8. The method of claim 5, wherein component a) and component b) are added separately to the system being treated.

9. The method of claim 5, wherein at least 0.1 ppm of the synergistic antimicrobial composition is added to the system being treated.

10. The method of claim 5, wherein between about 0.05 ppm and 1000 ppm of component a) and between about 0.01 ppm and 10 ppm of component b) are added to the system being treated.

11. The method of claim 5, wherein said effective amount is that amount which results in a Kull value of less than 1.

12. The method of claim 5, wherein said chlorinated isocyanurate is dichloroisocyanurate and said bromide compound is sodium bromide.

13. A method of inhibiting microbial growth on an article of manufacture which comprises applying to said article an effective amount of a synergistic antimicrobial combination comprising:
   a) 4,5-dichloro-2-N-octyl-4-isothiazolin-3-one; and
   b) a mixture of i) a chlorinated isocyanurate and ii) a bromide compound; wherein the weight ratio of a) to b), on an active basis, ranges between about 1:1 and 1500:1, and the weight ratio of i) to ii), on an active basis, ranges between about 3:1 and 20:1.

14. The method of claim 13, wherein the weight ratio of a) to b), on an active basis, ranges between about 5:1 and 1220:1; and the weight ration of i) to ii) ranges between about 5:1 and 19:1.

15. The method of claim 13, wherein component a) and component b) are applied together as a single composition to the article being treated.

16. The method of claim 13 wherein component a) and component b) are applied separately to the article being treated.

17. The method of claim 13, wherein at least 0.1 ppm of the synergistic antimicrobial composition is applied to the article being treated.

18. The method of claim 13, wherein between about 0.05 ppm and 1000 ppm of component a) and between about 0.01 ppm and 10 ppm of component b) are applied to the article being treated.

19. The method of claim 13, wherein said effective amount is that amount which results in a Kull value of less than 1.

20. The method of claim 13, wherein said chlorinated isocyanurate is dichloroisocyanurate and said bromide compound is sodium bromide.

* * * * *